United States Patent
Liu et al.

(10) Patent No.: US 11,241,161 B2
(45) Date of Patent: Feb. 8, 2022

(54) METHOD, DEVICE AND SYSTEM FOR MEASURING PHYSIOLOGICAL STATE INFORMATION BASED ON CHANNEL STATE INFORMATION

(71) Applicant: Industrial Technology Research Institute, Hsinchu (TW)

(72) Inventors: Chia-Lung Liu, Hsinchu County (TW); Chai-Hien Gan, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 89 days.

(21) Appl. No.: 16/232,519

(22) Filed: Dec. 26, 2018

(65) Prior Publication Data
US 2020/0178835 A1 Jun. 11, 2020

(30) Foreign Application Priority Data

Dec. 11, 2018 (TW) .................. 107144441

(51) Int. Cl.
*A61B 5/05* (2021.01)
*A61B 5/08* (2006.01)
(Continued)

(52) U.S. Cl.
CPC ............... *A61B 5/05* (2013.01); *A61B 5/024* (2013.01); *A61B 5/0816* (2013.01); *G01S 13/003* (2013.01); *G01S 13/88* (2013.01)

(58) Field of Classification Search
CPC ....... A61B 5/0816; A61B 5/024; G01S 13/88; G01S 13/003
See application file for complete search history.

(56) References Cited

U.S. PATENT DOCUMENTS

2008/0077015 A1  3/2008 Boric-Lubecke et al.
2015/0297142 A1* 10/2015 De Jaam .............. A61B 5/7278
                                                                 600/407
(Continued)

FOREIGN PATENT DOCUMENTS

CN   102046076 A   5/2011
CN   105232022 A   1/2016
(Continued)

OTHER PUBLICATIONS

Wang et al., "PhaseBeat: Exploiting CSI Phase Data for Vital Sign Monitoring with Commodity WiFi Devices", 2017 IEEE 37th International Conference on Distributed Computing Systems, 2017, pp. 1230-1239 (Year: 2017).*

(Continued)

*Primary Examiner* — Thomas M Hammond, III (57) ABSTRACT

A method, a device, and a system for measuring physiological state information based on channel state information are provided. The method includes: respectively transmitting, by at least two transmitting antennas of a transmitter, a measurement signal. Respectively receiving, by at least two receiving antennas of a receiver, a reflected signal reflected the measurement signal through a target object. Obtaining, by the receiver, channel state information (CSI) between the transmitting antennas and the receiving antennas according to the reflected signals. Receiving, by a computing device, the CSI transmitted by the receiver and obtaining physiological state information of the target object according to the CSI.

12 Claims, 8 Drawing Sheets

(51) Int. Cl.
*G01S 13/88* (2006.01)
*G01S 13/00* (2006.01)
*A61B 5/024* (2006.01)

(56) References Cited

U.S. PATENT DOCUMENTS

| | | | |
|---|---|---|---|
| 2016/0377704 | A1 | 12/2016 | Harash et al. |
| 2017/0300650 | A1* | 10/2017 | Margon ............... G16H 40/67 |
| 2019/0097865 | A1* | 3/2019 | Xu ..................... H04W 72/0413 |
| 2019/0175074 | A1* | 6/2019 | Zhang ..................... H04B 7/22 |
| 2019/0178980 | A1* | 6/2019 | Zhang ..................... A61B 5/02 |
| 2020/0022607 | A1* | 1/2020 | Pratt ..................... A61B 5/6891 |
| 2020/0113445 | A1* | 4/2020 | Gigie ..................... A61B 5/1115 |

FOREIGN PATENT DOCUMENTS

| | | | |
|---|---|---|---|
| CN | 106175767 A | * | 12/2016 |
| CN | 106725488 A | | 5/2017 |
| CN | 106821347 A | | 6/2017 |
| CN | 110301917 A | * | 10/2019 |
| JP | 2017129558 A | | 7/2017 |
| JP | 2018187129 A | | 11/2018 |
| WO | WO 2017/156492 A1 | | 9/2017 |

OTHER PUBLICATIONS

Chao Yang, Contact-free Vital Sign Monitoring Using Phase Difference of Channel State Information, Dec. 16, 2017, Thesis submitted to the Graduate Faculty of Auburn University (Year: 2017).*

Japan Patent Office, Office Action, Patent Application Serial No. 2019-095262, dated Jul. 28, 2020, Japan.

Taiwan Patent Office, Office Action, Patent Application Serial No. 107144441, dated May 28, 2019, Taiwan.

Liu et al., "Tracking Vital Signs During Sleep Leveraging Off-the-shelf WiFi," MobiHoc 2015, Jun. 2015, 11 pages, ACM, US.

Abdelnasser et al., "UbiBreathe: A Ubiquitous non-Invasive WiFi-based Breathing Estimator," MobiHoc 2015, May 2015, 11 pages, ACM, US.

Mao et al., "Smart Homes that Monitor Breathing and Heart Rate," CHI 2015, Apr. 2015, 10 pages, ACM, US.

Wang et al., "PhaseBeat: Exploiting CSI Phase Data for Vital Sign Monitoring with Commodity WiFi Devices," 2017 IEEE 37th International Conference on Distriubted Computing Systems, 2017, pp. 1230-1239, IEEE, US.

Chen et al., "TR-Breath: Time Reversal Breathing Rate Estimation and Detection," Transactions on Biomedical Engineering, 2016, pp. 1-14, IEEE, US.

Kao et al., Vital sign detection using 60-GHz Doppler radar system, IEEE MTT-S International Microwave Symposium Digest, 2012, 4 pages, IEEE, US.

Wang et al., "Human Respiration Detection with Commodity WiFi Devices: Do User Location and Body Orientation Matte?" IEEE UBICOMP 2016, Sep. 2016, pp. 25-36, ACM, US.

Wu et al., "Vital-Sign Detection Doppler Radar Based on Phase Locked Self-Injection Oscillator," 2012, 3 pages, IEEE, US.

* cited by examiner

FIG. 8

METHOD, DEVICE AND SYSTEM FOR MEASURING PHYSIOLOGICAL STATE INFORMATION BASED ON CHANNEL STATE INFORMATION

CROSS REFERENCE TO RELATED APPLICATIONS

This application claims priority from Taiwan Patent Application No. 107144441, filed on Dec. 11, 2018, the disclosure of which is incorporated herein by reference in its entirety.

TECHNICAL FIELD

The present disclosure relates to a method, device and system for measuring physiological state information, and more particularly, it relates to a method, device and system for measuring physiological state information based on channel state information.

BACKGROUND

Respiration rate is the number of breaths a person takes per minute. Respiration rates can increase or decrease with fever, illness, and other medical conditions, and thus, a patient's respiration rate is frequently monitored as a means of analyzing the patient's medical state of health. Respiration rate can be represented as a number of breaths per minute or as a frequency (e.g., a frequency of 1 Hz corresponds to 60 breaths per minute). A patient's respiration rate can be measured manually (e.g., by having a clinician count the number of breaths that the patient takes over a period of time) or via respiration measurement apparatuses.

However, current respiration measurement apparatuses are mostly contact devices. Subjects (e.g., elderly people) may experience nuisance of use due to inconvenient wear of the respiration measurement apparatuses. The use of contactless respiration measurements has been one of the most popular research techniques in recent years.

SUMMARY

The following summary is illustrative only and is not intended to be limiting in any way. That is, the following summary is provided to introduce concepts, highlights, benefits and advantages of the novel and non-obvious techniques described herein. Select, not all, implementations are described further in the detailed description below. Thus, the following summary is not intended to identify essential features of the claimed subject matter, nor is it intended for use in determining the scope of the claimed subject matter.

Therefore, the main purpose of the present disclosure is to provide a method, device and system for measuring physiological state information based on channel state information to improve the above disadvantages.

In an embodiment, a method for measuring physiological state information based on channel state information is provided in the disclosure. The method comprises: respectively transmitting, by at least two transmitting antennas of a transmitter, a measurement signal; respectively receiving, by at least two receiving antennas of a receiver, a reflected signal reflected the measurement signal through a target object; obtaining, by the receiver, channel state information (CSI) between the transmitting antennas and the receiving antennas according to the reflected signals; and receiving, by a computing device, the CSI transmitted by the receiver and obtaining physiological state information of the target object according to the CSI.

In some embodiments, a first receiving antenna of the receiving antennas receives a first reflected signal and a second reflected signal, and a second receiving antenna of the receiving antennas receives a third reflected signal and a fourth reflected signal; wherein the first reflected signal is generated by reflecting a first measurement signal transmitted by a first transmitting antenna of the transmitting antennas through the target object, and the second reflected signal is generated by reflecting a second measurement signal transmitted by a second transmitting antenna of the transmitting antennas through the target object; and wherein the third reflected signal is generated by reflecting the first measurement signal transmitted by the first transmitting antenna through the target object, and the fourth reflected signal is generated by reflecting the second measurement signal transmitted by the second transmitting antenna through the target object.

In some embodiments, the step of obtaining physiological state information of the target object according to the CSI further comprises: calculating a first phase difference between the first reflected signal and the third reflected signal; calculating a second phase difference between the second reflected signal and the fourth reflected signal; and obtaining the physiological state information of the target object according to a difference of a channel response between the first phase difference and the second phase difference.

In some embodiments, the step of obtaining the physiological state information of the target object according to the difference of the channel response further comprises: obtaining the differences of the channel response corresponding to a time period; transforming the differences of the channel response into spectrograms corresponding to a plurality of subcarriers; and determining the physiological state information according to a frequency corresponding to a highest peak in the spectrograms.

In some embodiments, the differences of the channel response corresponding to the time period is transformed into a first spectrogram and a second spectrogram corresponding to the subcarriers by using two frequency analysis modes, and the step of determining the physiological state information according to a frequency corresponding to the highest peak in the spectrograms further comprises: obtaining a first frequency corresponding to the highest peak of a vertical axis in the first spectrogram of each subcarrier and a second frequency corresponding to the highest peak of the vertical axis in the second spectrogram of each subcarrier; determining whether a frequency difference between the first frequency and the second frequency of a first subcarrier of the subcarriers exceeds a threshold; removing the first subcarrier when determining that the frequency difference exceeds the threshold; reserving the first subcarrier when determining that the frequency difference does not exceed the threshold; and determining the physiological state information according to the frequencies corresponding to the highest magnitude peak in the spectrograms corresponding to the reserved subcarriers.

In an embodiment, a system for measuring physiological state information based on channel state information is provided. The system comprises a transmitter, a receiver and a computing device. The transmitter is configured with at least two transmitting antennas, wherein the at least two transmitting antennas transmit a measurement signal, respectively. The receiver is configured with at least two receiving antennas, wherein each of the receiving antennas receives a reflected signal reflected the measurement signal through a target object, and the receiver obtains channel state information (CSI) between the transmitting antennas and the receiving antennas according to the reflected signals. The computing device is coupled to the receiver and receives the CSI and obtaining physiological state information of the target object according to the CSI.

In an embodiment, a device for measuring physiological state information based on channel state information is provided. The device comprises one or more processors and one or more computer storage media for storing one or more computer-readable instructions. The processor is configured to drive the computer storage media to execute the following tasks: receiving channel state information (CSI) between at least two transmitting antennas of a transmitter and at least two receiving antennas of a receiver, wherein the CSI is transmitted from the receiver and is obtained by the receiver according to reflected signals; the reflected signals are generated by reflecting measurement signals transmitted by the transmitting antennas of the transmitter through a target object, and the reflected signals are received by the antennas of the receiver; and obtaining physiological state information of the target object according to the CSI.

In an embodiment, a method for measuring physiological state information based on channel state information is provided. The method comprises: receiving channel state information (CSI) between at least two transmitting antennas of a transmitter and at least two receiving antennas of a receiver, wherein the CSI is transmitted from the receiver and is obtained by the receiver according to reflected signals; the reflected signals are generated by reflecting measurement signals transmitted by the transmitting antennas of the transmitting antennas through a target object, and the reflected signals are received by the antennas of the receiver; and obtaining physiological state information of the target object according to the CSI.

BRIEF DESCRIPTION OF DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It should be appreciated that the drawings are not necessarily to scale as some components may be shown out of proportion to the size in actual implementation in order to clearly illustrate the concept of the present disclosure.

DETAILED DESCRIPTION

Various aspects of the disclosure are described more fully below with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects. Furthermore, like numerals refer to like elements throughout the several views, and the articles "a" and "the" includes plural references, unless otherwise specified in the description.

It should be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion. (e.g., "between" versus "directly between", "adjacent" versus "directly adjacent", etc.).

Figure 1:
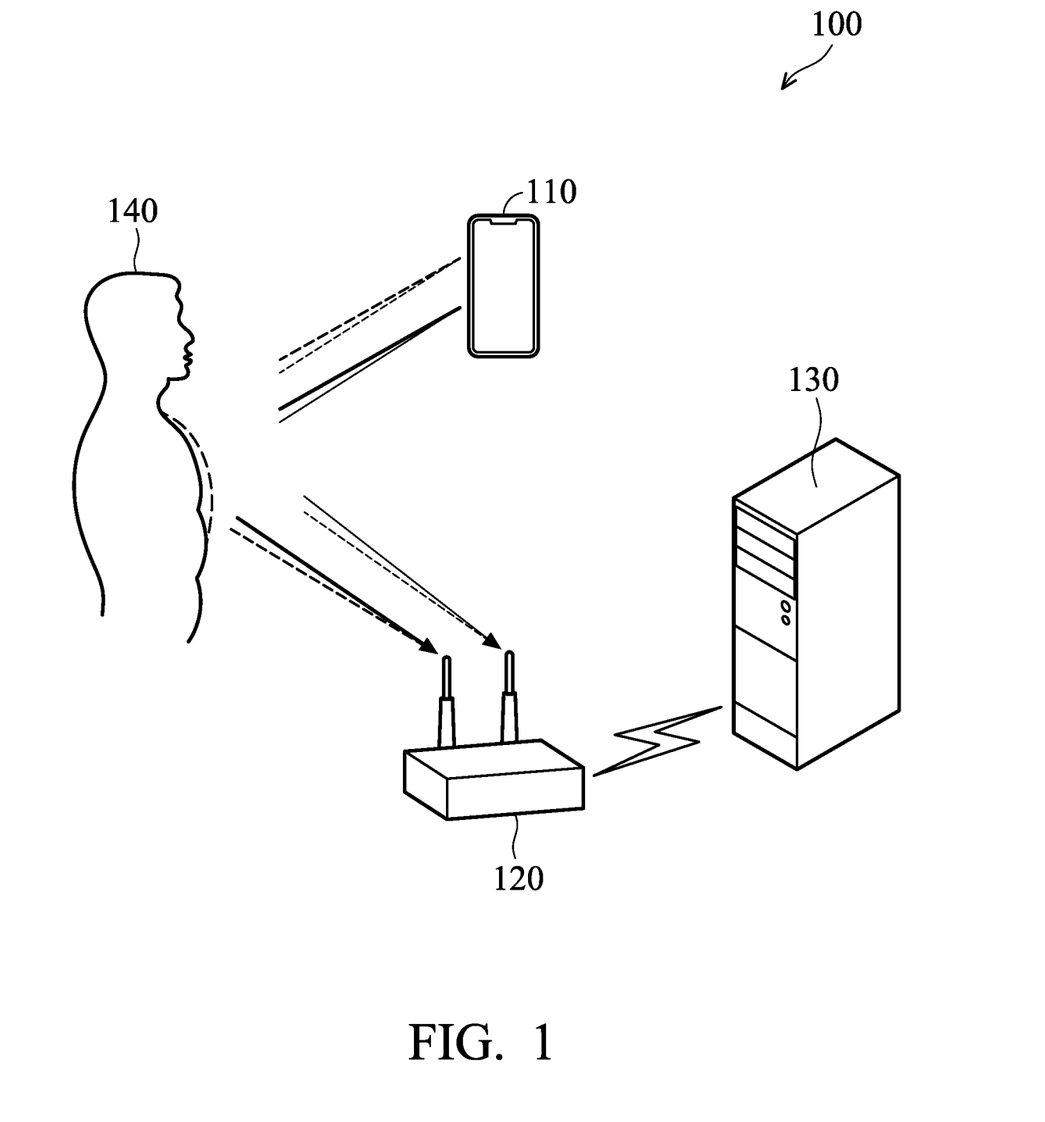
FIG. 1 shows a schematic diagram of a system for measuring physiological state information based on channel state information according to one embodiment of the present disclosure.

FIG. 1 shows a schematic diagram of a system 100 for measuring physiological state information based on channel state information according to one embodiment of the present disclosure. The system 100 comprises a transmitter 110, a receiver 120 and a computing device 130. The transmitter 110 and the receiver 120 are positioned adjacent to a target object 140, wherein the distance between the transmitter 110 and the target object 140 and between the receiver 120 and the target object 140 is, for example, not more than 5 meters.

The transmitter 110 has a plurality of transmitting antennas, wherein each of the transmitting antennas can transmit a measurement signal to the target object 140. The receiver 120 has a plurality of receiving antennas, wherein each of the receiving antennas receives reflected signals reflected through the target object 140. The transmitter 110 and/or the receiver 120 can be fixed or mobile and include various components that communicate with the computing device 130 and transmit and receive data and/or various control information to and from the computing device 130. The transmitter 110 and the receiver 120 can be a terminal device, a mobile station (MS), a mobile terminal (MT), a user terminal (UT), a subscriber station (SS), a wireless device, an access point (AP) or a processing server (PS). In an embodiment, the transmitter 110 and the receiver 120 may transmit and/or receive signals using a wireless communication technology such as a wireless local area network (WLAN), Bluetooth, ZigBee, Worldwide Interoperability for Microwave Access (WiMAX), Third Generation Of Wireless Mobile Telecommunications Technology (3G), Fourth Generation Of Cellular Network Technology (4G), Long Term Evolution (LTE) or LTE-Advanced. In one embodiment, the measurement signals and/or the received signals include signals on a plurality of subcarriers.

The computing device 130 is coupled to the receiver 120 and can transmit data to or receive data from the receiver 120 over a wired network or wireless communication, and includes a processor and a memory that may store the program. The computing device 130 receives the reflected signals transmitted by the receiver 120, obtains channel state information (CSI) between the transmitting antennas of the transmitter 110 and the receiving antennas of the receiver 120 according to the reflected signals, and obtains physiological state information of the target object 140 according to the CSI.

The types of computing device 130 range from small handheld devices, such as mobile telephones and handheld computers, to large mainframe systems, such as mainframe computers. Examples of handheld computers include personal digital assistants (PDAs) and notebooks. In another embodiment, the computing device 130 may be used with components, systems, sub-systems, and/or devices other than those that are depicted herein. For example, the computing device 130 can be integrated with the receiver 120 as a device.

It should be understood that the computing device 130 shown in FIG. 1 is an example for one suitable system 100 architecture measuring physiological state information based on channel state information. Each of the components shown in FIG. 1 may be implemented through any type of computing device, such as the computing device 800 described with reference to FIG. 8, for example.

Figure 2:
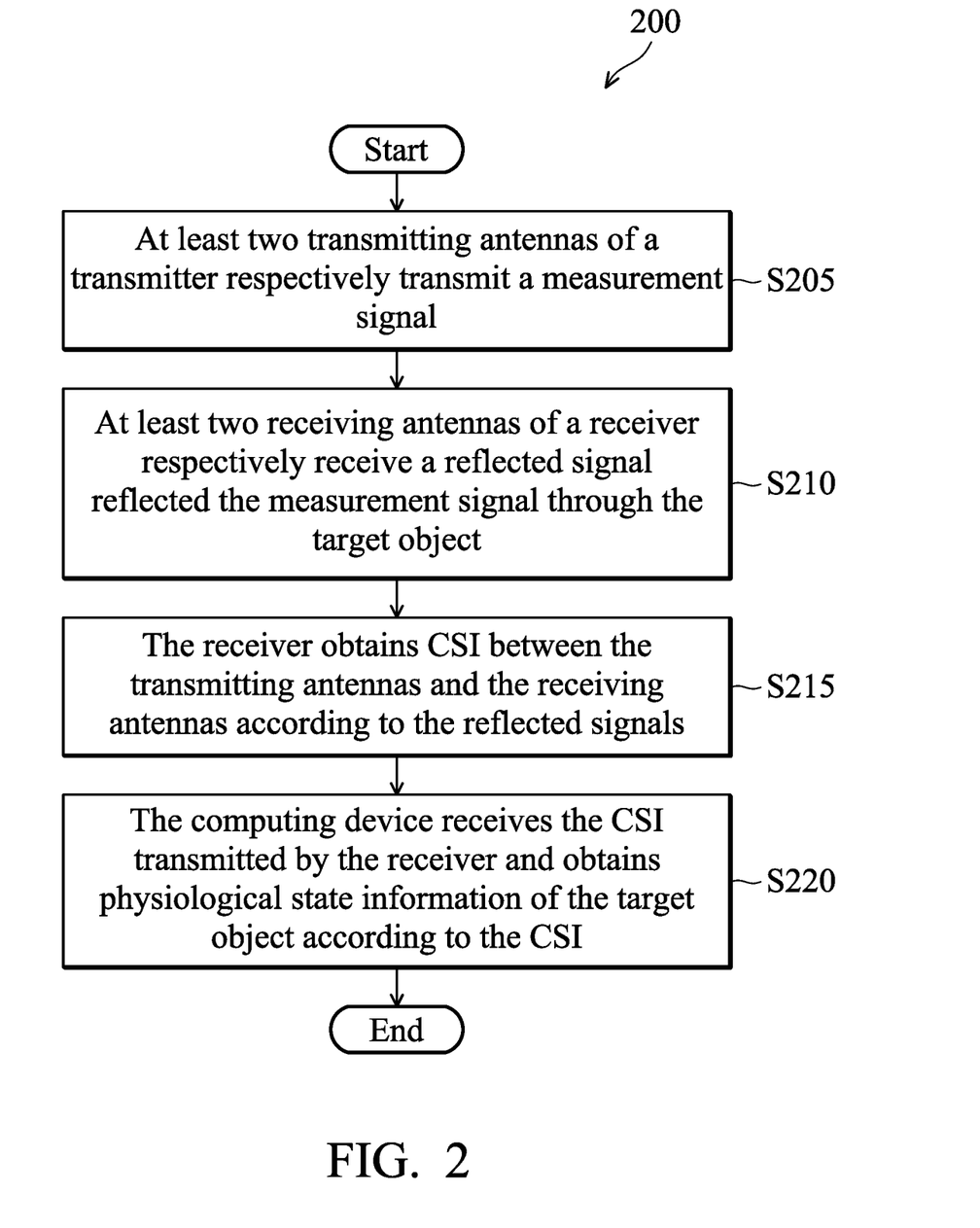
FIG. 2 is a flowchart illustrating a method for measuring physiological state information based on channel state information according to an embodiment of the present disclosure.

FIG. 2 is a flowchart illustrating a method 200 for measuring physiological state information based on channel state information according to an embodiment of the present disclosure. The method can be implemented in the system 100 for measuring physiological state information based on channel state information as shown in FIG. 1.

In step S205, at least two transmitting antennas of a transmitter Tx respectively transmit a measurement signal. Specifically, the at least two transmitting antennas of the transmitter Tx may directly transmit the measurement signal to the target object, or may transmit the measurement signal not in the direction of the target object. The measurement signals not emitted in the direction of the target object may be reflected to the target object through other objects. For example, the transmitter Tx emits a measurement signal toward a wall, and the wall reflects the measurement signal to the target object. Next, in step S210, at least two receiving antennas of a receiver Rx respectively receive a reflected signal reflected the measurement signal through the target object. Specifically, the reflected signal received by the receiver Rx may be a signal directly reflected by the target object, or may be a reflected signal reflected by the target object and then reflected through other objects (for example, an object such as a wall or a table).

In step S215, the receiver Rx obtains channel state information (CSI) between the transmitting antennas and the receiving antennas according to the reflected signals. In step S220, the computing device 130 receives the CSI transmitted by the receiver Rx and obtains physiological state information of the target object according to the CSI.

Figure 3:
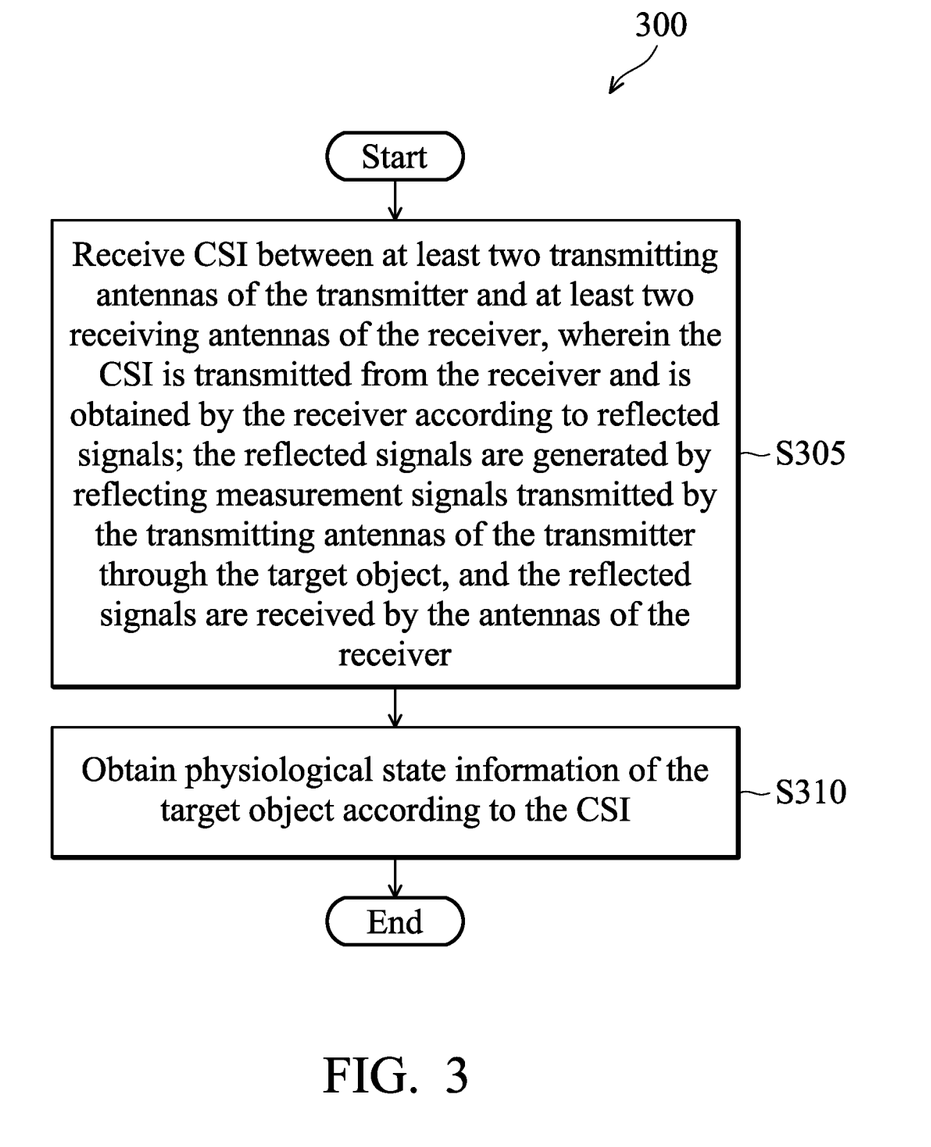
FIG. 3 is a flowchart illustrating a method for measuring physiological state information based on channel state information according to an embodiment of the present disclosure.

FIG. 3 is a flowchart illustrating a method 300 for measuring physiological state information based on channel state information according to an embodiment of the present disclosure. The method can be executed by a processor of the computing device 130 as shown in FIG. 1.

In step S305, the computing device 130 receives channel state information (CSI) between at least two transmitting antennas of the transmitter 110 and at least two receiving antennas of the receiver 120, wherein the CSI is transmitted from the receiver 120 and is obtained by the receiver 120 according to reflected signals; the reflected signals are generated by reflecting measurement signals transmitted by the transmitting antennas of the transmitter 110 through the target object, and the reflected signals are received by the antennas of the receiver 120. In step S310, the computing device 130 obtains physiological state information of the target object according to the CSI.

The following describes the details in step S220 and S310 how the computing device 130 obtains the physiological state information of the target object based on the CSI.

Figure 4:
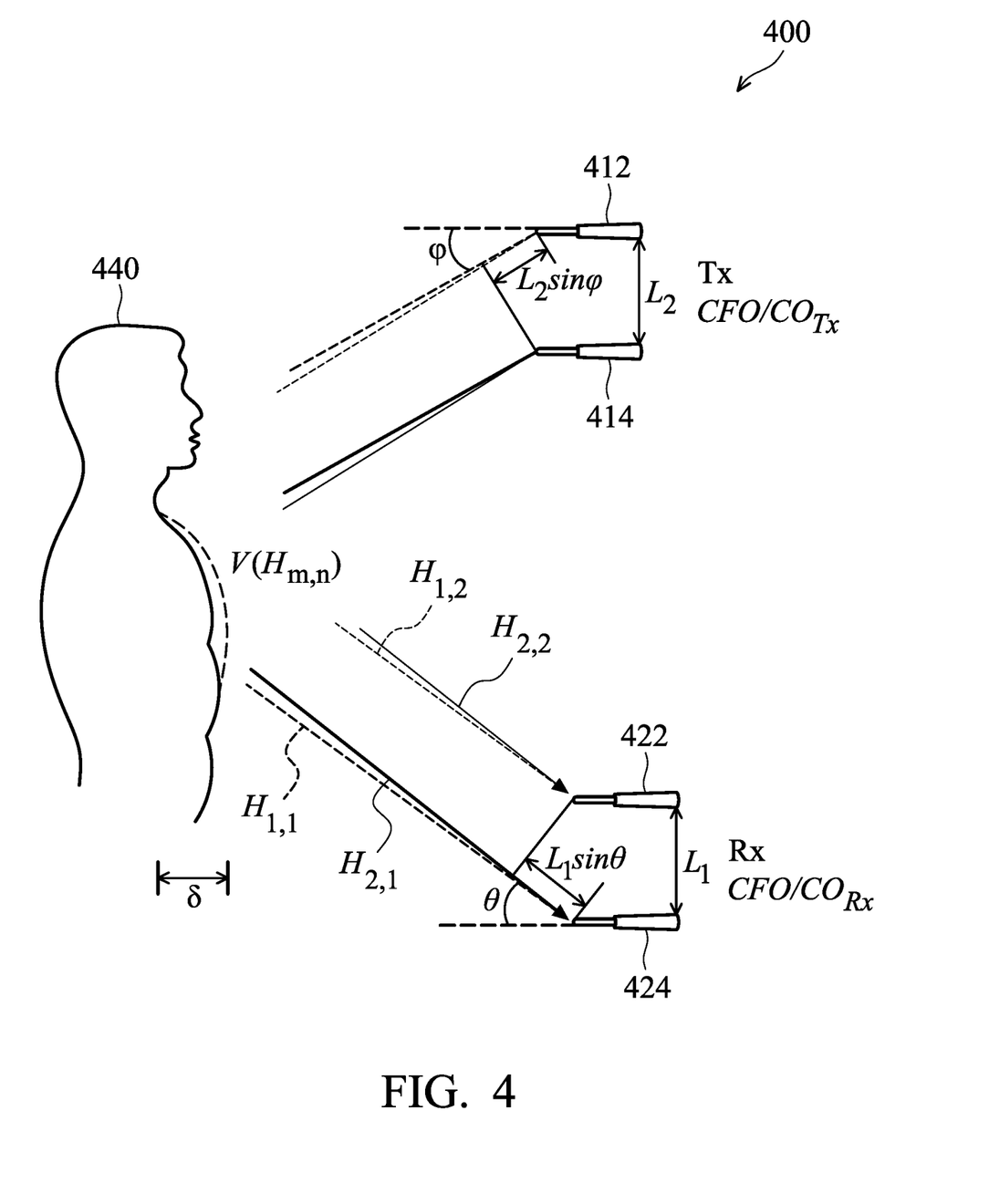
FIG. 4 is a schematic diagram illustrating a system for measuring physiological state information based on channel state information according to an embodiment of the present disclosure.

FIG. 4 is a schematic diagram illustrating a system 400 for measuring physiological state information based on channel state information according to an embodiment of the present disclosure. FIG. 4 more clearly describes the transmission between the transmitting antennas of the transmitter Tx and the receiving antennas of the receiver Rx. It should be noted that although the number of antennas of the transmitter Tx and the receiver Rx in FIG. 4 used in this example is two antennas, it should not be limited in the disclosure. In other words, as long as the receiver Rx selects any two (or at least two) receiving antennas to receive the reflected signals, and the reflected signals are generated by the target object reflecting the measurement signal transmitted by any two (or at least two) of the transmitting antennas of the transmitter Tx, the methods mentioned in disclosure can be achieved.

As shown in FIG. 4, a first transmitting antenna 412 of the transmitter Tx transmits a first measurement signal to the target object 440, and a second transmitting antenna 414 of the transmitter Tx transmits a second measurement signal 414 to the target object 440, wherein the distance between the first transmitting antenna 412 and the second transmitting antenna 414 is $L_2$, and the angle between the measurement signal and the horizontal plane is $\varphi$. The range between the rise and fall of the chest of the target object 440 is $\delta$.

The first receiving antenna 422 of the receiver Rx receives a first reflected signal and a second reflected signal, and the second receiving antenna 424 of the receiver Rx receives a third reflected signal and a fourth reflected signal, wherein the distance between the first receiving antenna 422 and the second receiving antenna 424 is $L_1$, and the angle between the reflected signal and the horizontal plane is $\theta$. The first reflected signal is generated by reflecting the first measurement signal transmitted by the first transmitting antenna 412 through the target object 440, and the second reflected signal is generated by reflecting the second measurement signal transmitted by the second transmitting antenna 414 through the target object 440. The third reflected signal is generated by reflecting the first measurement signal transmitted by the first transmitting antenna 412 through the target object 440, and the fourth reflected signal is generated by reflecting the second measurement signal transmitted by the second transmitting antenna 414 through the target object 440.

Therefore, the receiver Rx may obtain the CSI between the transmitter (the first transmitting antenna 412 and the second transmitting antenna 414) and the receiver (the first receiving antenna 422 and the second receiving antenna 424) at time t according to the reflected signals received at time t. The CSI at time t can be expressed as follows:

$$H_{1,1} = CFO/CO_{Tx} + L_2 \sin \varphi + V_t(H_{1,1}) + L_1 \sin \theta + CFO/CO_{Rx} \quad (1)$$

$$H_{1,2} = CFO/CO_{Tx} + L_2 \sin \varphi + V_t(H_{1,2}) + CFO/CO_{Rx} \quad (2)$$

$$H_{2,1} = CFO/CO_{Tx} + V_t(H_{2,1}) + L_1 \sin \theta + CFO/CO_{Rx} \quad (3)$$

$$H_{2,2} = CFO/CO_{Tx} + V_t(H_{2,2}) + CFO/CO_{Rx} \quad (4)$$

wherein $H_{m,n}$ represents the CSI (also referred to as channel response) between the $m^{th}$ transmitting antenna of the transmitter Tx and the $n^{th}$ receiving antenna of the receiver Rx, $CFO/CO_{Tx}$ is the phase shift caused by the carrier frequency offset (CFO) and the clock offset (CO) of the transmitter, and the $CFO/CO_{Rx}$ is the phase shift caused by the CFO and the CO of the receiver. $L_2 \sin \varphi$ and $L_1 \sin \theta$ are measured noises, and $V_t(H_{m,n})$ is the channel response phase at time t.

Then, the computing device 130 calculates a first phase difference $\Delta V_t(H_1) + L_1 \sin \theta$ between the CSI $H_{1,1}$ and the CSI $H_{1,2}$ (i.e., the difference between equation (1) and equation (2)), and calculate a second phase difference $\Delta V_t(H_2) + L_1 \sin \theta$ between the CSI $H_{2,1}$ and the CSI $H_{2,2}$ (i.e., the difference between equation (3) and equation (4)), wherein $\Delta V_t(H_1)$ is the difference between $V_t(H_{1,1})$ and $V_t(H_{1,2})$ (i.e., $\Delta V_t(H_1) = V_t(H_{1,1}) - V_t(H_{1,2})$), and $\Delta V_t(H_2)$ is the difference between $V_t(H_{2,1})$ and $V_t(H_{2,2})$ (i.e., $\Delta V_t(H_2) = V_t(H_{2,1}) - V_t(H_{2,2})$). The computing device 130 calculates the difference $\Delta V_t(H)$ of the channel response between the first phase difference and the second phase difference at time t. In other words, a difference $\Delta V_t(H)$ of the channel response is the difference between $\Delta V_t(H_1)$ and $\Delta V_t(H_2)$. The computing device 130 then collects the differences $\Delta V_t(H)$ of the channel response for a time period to obtain physiological state information.

The following describes in details how the computing device 130 obtains the physiological state information of the target object using the differences $\Delta V_t(H)$ of the channel response for a time period. This part will be described in terms of different physiological states and physiological state information.

Figure 5:
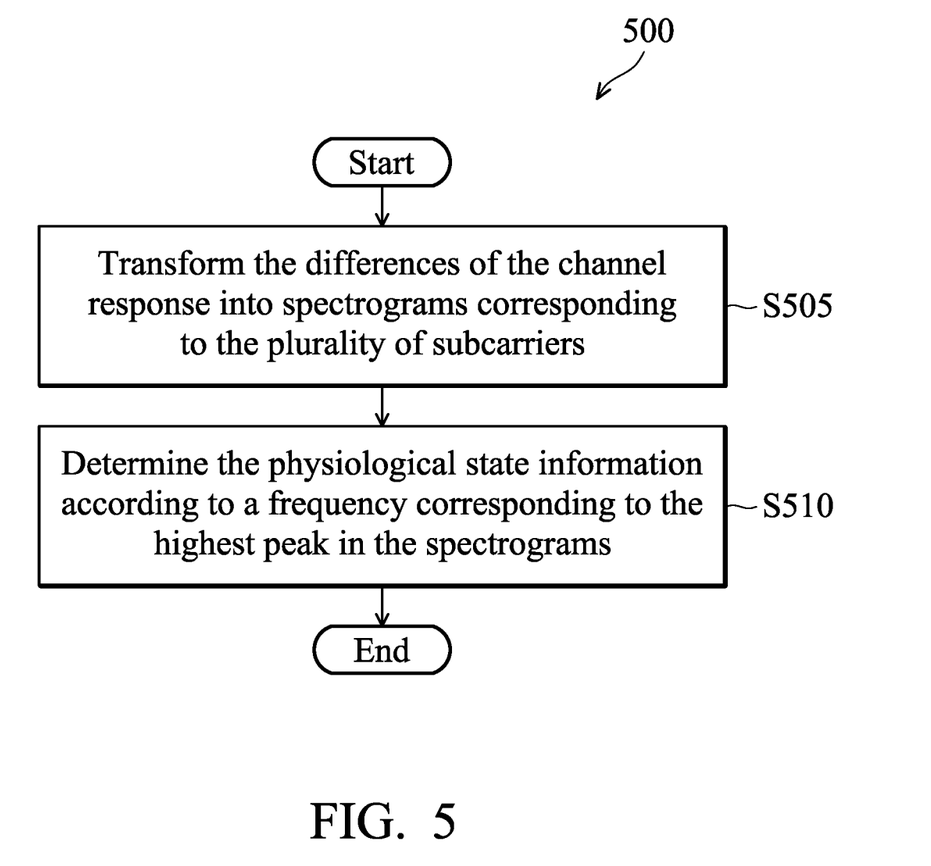
FIG. 5 is a flowchart illustrating a method for obtaining physiological state information of a target object according to the difference of the channel response for a time period in accordance with one embodiment of the present disclosure.

FIG. 5 is a flowchart illustrating a method 500 for obtaining physiological state information of a target object according to the difference of the channel response for a time period in accordance with one embodiment of the present disclosure. In this embodiment, the physiological state is breathing and the physiological state information is respiratory frequency. The time period is, for example, the length of time during which the physiological state information (in this embodiment, the physiological state information is the respiratory rate) is measured. For example, if the time period is 1 minute, the respiratory rate within the minute is estimated once per minute. The transmitter may transmit a plurality of measurement signals and the receiver may receive a plurality of reflected signals reflected the plurality of measurement signals during the time period. For example, the transmitter may transmit a measurement signal per 10 ms and the receiver may receive a reflected signal per 10 ms.

In an embodiment, before the start of the process, the computing device 130 has obtained the differences of the channel response corresponding to a time period. In step S505, the computing device 130 transforms the differences of the channel response into spectrograms corresponding to the plurality of subcarriers, wherein the differences of the channel response are transformed into the spectrograms through Fourier transform or other frequency analysis manners (for example, MUltiple SIgnal Classification (MUSIC), Hilbert-Huang Transform (HHT), and Discrete Wavelet Transform (DWT)). In step S510, the computing device 130 determines the physiological state information according to a frequency corresponding to the highest peak in the spectrograms. Specifically, the computing device 130 may overlay the spectrogram of each subcarrier and consider a frequency corresponding to the highest peak in the overlapping spectrograms as the respiratory frequency.

Figure 6:
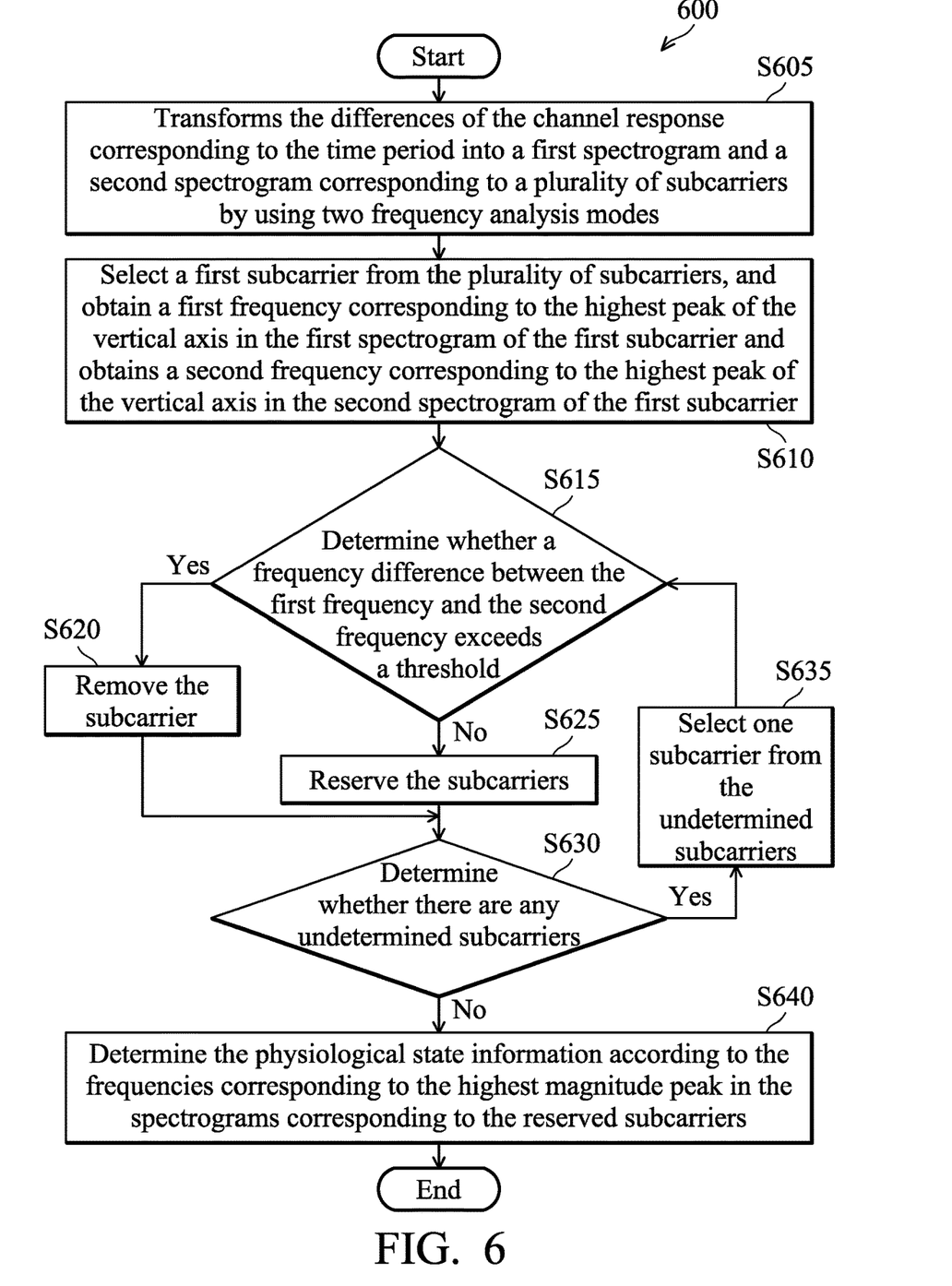
FIG. 6 is a flowchart illustrating a method for obtaining physiological state information of a target object according to the difference of the channel response for a time period in accordance with one embodiment of the present disclosure.

FIG. 6 is a flowchart illustrating a method 600 for obtaining physiological state information of a target object according to the difference of the channel response for a time period in accordance with one embodiment of the present disclosure. In this embodiment, the physiological state is breathing or heartbeat, and the physiological state information is respiratory frequency or heartbeat frequency.

In an embodiment, before the start of the process, the computing device 130 has obtained the differences of the channel response corresponding to a time period. In step S605, the computing device 130 transforms the differences of the channel response corresponding to the time period into a first spectrogram and a second spectrogram corresponding to a plurality of subcarriers by using two frequency analysis modes, wherein the two frequency analysis modes may be any two of Fourier transform, Music, HHT, and DWT, and other frequency analysis manners. In an embodiment, the vertical axes of the first spectrogram and the second spectrogram are magnitude, and the horizontal axes are frequency. In step S610, the computing device 130 selects a first subcarrier from the plurality of subcarriers, and obtains a first frequency corresponding to the highest peak of the vertical axis (magnitude) in the first spectrogram of the first subcarrier and obtains a second frequency corresponding to the highest peak of the vertical axis (magnitude) in the second spectrogram of the first subcarrier. In step S615, the computing device 130 determines whether a frequency difference between the first frequency and the second frequency exceeds a threshold. When the computing device 130 determines that the frequency difference exceeds the threshold value ("Yes" in step S615), in step S620, the computing device 130 removes the subcarrier. When the computing device 130 determines that the frequency difference does not exceed the threshold ("No" in step S615), in step S625, the computing device 130 reserves the subcarriers. Next, in step S630, the computing device 130 determines whether there are any undetermined subcarriers. When there are still undetermined subcarriers ("Yes" in step S630), in step S635, the computing device 130 selects one subcarrier (e.g., the second subcarrier) from the undetermined subcarriers, and the process returns to step S615 (e.g., the computing device 130 determines whether a frequency difference between the first frequency and the second frequency of the second subcarrier exceeds the threshold). When the computing device 130 determines that there are no undetermined subcarriers ("No" in step S630), in step S640, the computing device 130 determines the physiological state information according to the frequencies corresponding to the highest magnitude peak in the spectrograms corresponding to the reserved subcarriers. In an embodiment, the computing device 130 may multiply the first frequency and the second frequency of each reserved subcarrier, overlap the spectrums after multiplying the first frequency and the second frequency of each reserved subcarrier, and consider a frequency corresponding to the highest magnitude peak in the overlapping spectrograms as the respiratory rate or heartbeat frequency. In another embodiment, the computing device 130 may also select one spectrogram from the spectrograms after multiplying the first frequency and the second frequency of each reserved subcarrier. A frequency corresponding to the highest magnitude peak in this spectrogram is considered as the respiratory rate or heartbeat frequency. In an embodiment, the number of reserved subcarriers may be one or more.

Figure 7:
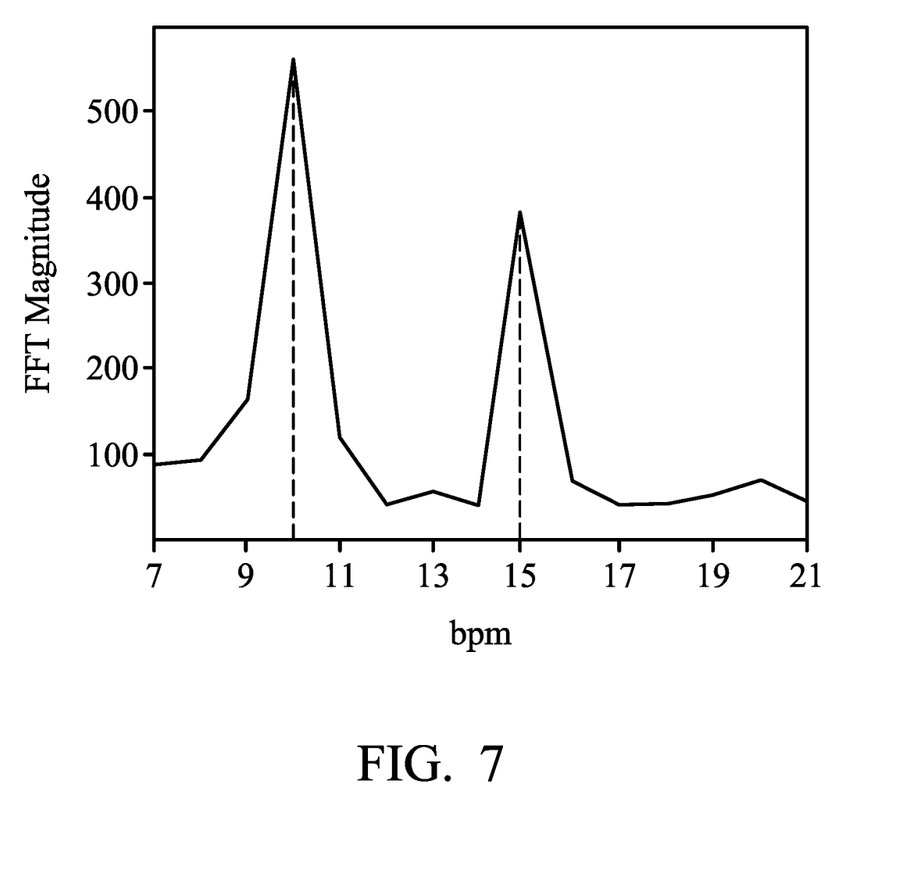
FIG. 7 is a schematic diagram illustrating the physiological state information of multiple subjects according to an embodiment of the present disclosure.

In another embodiment, the system can measure multiple subjects. The computing device 130 may select a first frequency corresponding to the first highest magnitude peak in the overlapping spectrogram as the physiological state information of the first subject, and then select a second frequency corresponding to the second highest magnitude peak as the physiological state information of the second subject. As shown in FIG. 7, a first frequency corresponding to the first highest magnitude peak is 10 bpm, and a second frequency corresponding to the second highest magnitude peak is 15 bpm. Therefore, the computing device 130 can determine that the respiratory frequencies of the first subject and the second subject are 10 and 15 bpm, respectively.

As described above, the method, device and system for measuring physiological state information based on channel state information provided in the disclosure can eliminate the CFO, CO and the measured noise by using the phase difference between the signals transmitted by the plurality of antennas of the contactless device to improve the accuracy of respiratory or heartbeat measurement techniques based on the CSI.

Figure 8:
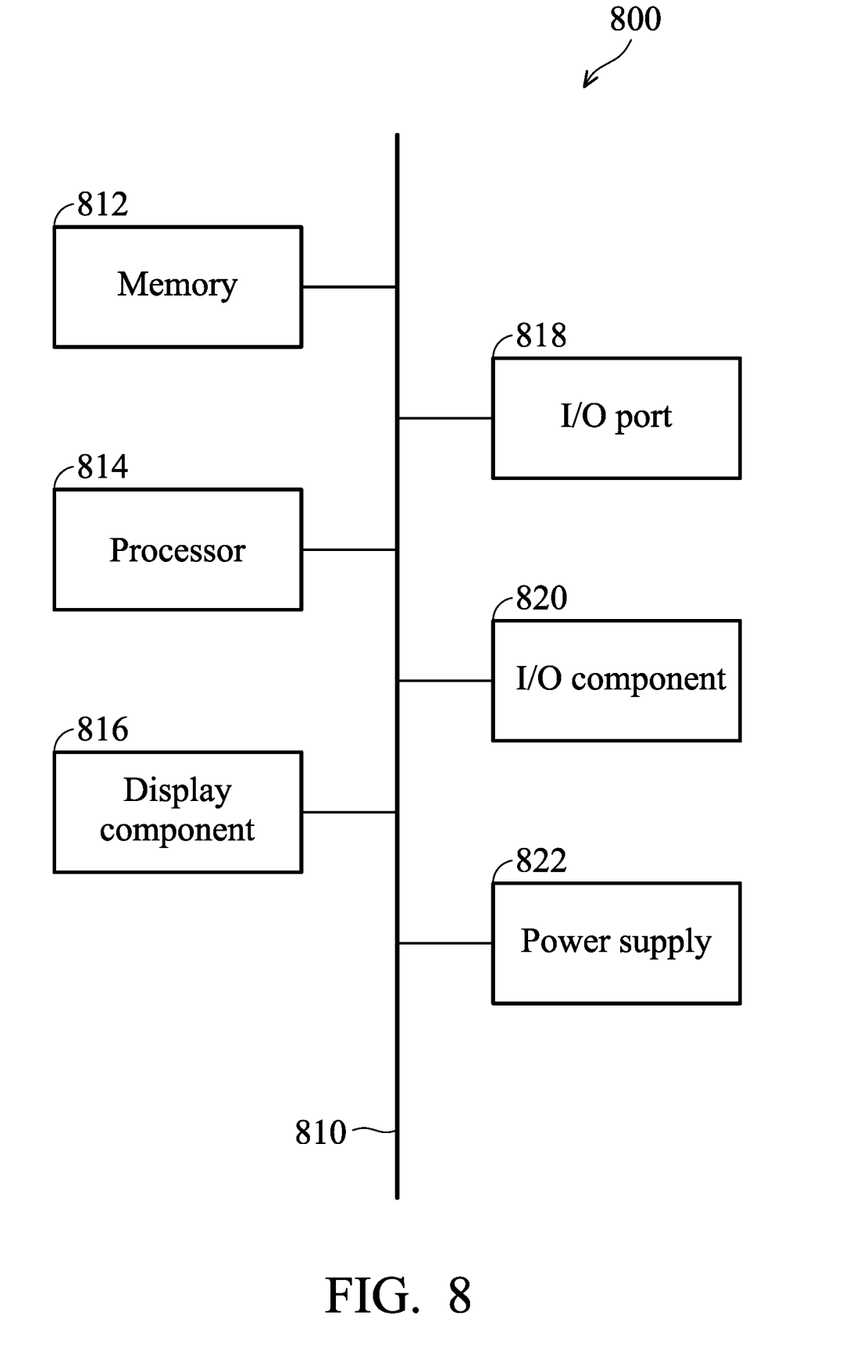
FIG. 8 illustrates an exemplary operating environment for implementing embodiments of the present disclosure.

Having described embodiments of the present disclosure, an exemplary operating environment in which embodiments of the present disclosure may be implemented is described below. Referring to FIG. 8, an exemplary operating environment for implementing embodiments of the present disclosure is shown and generally known as a computing device 800. The computing device 800 is merely an example of a suitable computing environment and is not intended to limit the scope of use or functionality of the disclosure. Neither should the computing device 800 be interpreted as having any dependency or requirement relating to any one or combination of components illustrated.

The disclosure may be realized by means of the computer code or machine-useable instructions, including computer-executable instructions such as program modules, being executed by a computer or other machine, such as a personal data assistant (PDA) or other handheld device. Generally, program modules may include routines, programs, objects, components, data structures, etc., and refer to code that performs particular tasks or implements particular abstract data types. The disclosure may be implemented in a variety of system configurations, including hand-held devices, consumer electronics, general-purpose computers, more specialty computing devices, etc. The disclosure may also be implemented in distributed computing environments where tasks are performed by remote-processing devices that are linked by a communication network.

With reference to FIG. 8, the computing device 800 may include a bus 810 that is directly or indirectly coupled to the following devices: one or more memories 812, one or more processors 814, one or more display components 816, one or more input/output (I/O) ports 818, one or more input/output components 820, and an illustrative power supply 822. The bus 810 may represent one or more kinds of busses (such as an address bus, data bus, or any combination thereof). Although the various blocks of FIG. 8 are shown with lines for the sake of clarity, and in reality, the boundaries of the various components are not specific. For example, the display component such as a display device may be considered an I/O component and the processor may include a memory.

The computing device 800 typically includes a variety of computer-readable media. The computer-readable media can be any available media that can be accessed by computing device 800 and includes both volatile and nonvolatile media, removable and non-removable media. By way of example, but not limitation, computer-readable media may comprise computer storage media and communication media. The computer storage media may include volatile and nonvolatile, removable and non-removable media implemented in any method or technology for storage of information such as computer-readable instructions, data structures, program modules or other data. The computer storage media may include, but not limit to, random access memory (RAM), read-only memory (ROM), electrically-erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by the computing device 800. The computer storage media may not comprise signal per se.

The communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, but not limitation, communication media includes wired media such as a wired network or direct-wired connection, and wireless media such as acoustic, RF, infrared and other wireless media or any combination thereof.

The memory 812 may include computer-storage media in the form of volatile and/or nonvolatile memory. The memory may be removable, non-removable, or a combination thereof. Exemplary hardware devices include solid-state memory, hard drives, optical-disc drives, etc. The computing device 800 includes one or more processors that read data from various entities such as the memory 812 or the I/O components 820. The presentation component(s) 816 present data indications to a user or other device. Exemplary presentation components include a display device, speaker, printing component, vibrating component, etc.

The I/O ports 818 allow the computing device 800 to be logically coupled to other devices including the I/O components 820, some of which may be embedded. Illustrative components include a microphone, joystick, game pad, satellite dish, scanner, printer, wireless device, etc. The I/O components 820 may provide a natural user interface (NUI) that processes gestures, voice, or other physiological inputs generated by a user. For example, inputs may be transmitted to an appropriate network element for further processing. A NUI may be implemented to realize speech recognition, touch and stylus recognition, face recognition, biometric recognition, gesture recognition both on screen and adjacent to the screen, air gestures, head and eye tracking, touch recognition associated with displays on the computing device 800, or any combination of. The computing device 800 may be equipped with depth cameras, such as stereoscopic camera systems, infrared camera systems, RGB camera systems, any combination of thereof to realize gesture detection and recognition. Furthermore, the computing device 800 may be equipped with accelerometers or gyroscopes that enable detection of motion. The output of the accelerometers or gyroscopes may be provided to the display of the computing device 800 to carry out immersive augmented reality or virtual reality.

Furthermore, the processor 814 in the computing device 800 can execute the program code in the memory 812 to perform the above-described actions and steps or other descriptions herein.

It should be understood that any specific order or hierarchy of steps in any disclosed process is an example of a sample approach. Based upon design preferences, it should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for measuring physiological state information based on channel state information, comprising:
   respectively transmitting, by at least two transmitting antennas of a transmitter, a measurement signal;
   respectively receiving, by at least two receiving antennas of a receiver, a reflected signal reflected the measurement signal through a target object;
   obtaining, by the receiver, channel state information (CSI) between the transmitting antennas and the receiving antennas according to the reflected signals, wherein the transmitting antennas comprises a first transmitting antenna and a second transmitting antenna, the receiving antennas comprises a first receiving antenna and a second receiving antenna, the CSI comprises first CSI between the first transmitting antenna and the first receiving antenna, second CSI between the first transmitting antenna and the second receiving antenna, third CSI between the second transmitting antenna and the first receiving antenna, and fourth CSI between the second transmitting antenna and the second receiving antenna; and
   receiving, by a computing device, the CSI transmitted by the receiver, and obtaining physiological state information of the target object according to a difference value between a difference between the first CSI and the second CSI and a difference between the third CSI and the fourth CSI,
   wherein the step of obtaining the physiological state information of the target object according to the difference of the channel response further comprises:
   obtaining the differences of the channel response corresponding to a time period;
   transforming the differences of the channel response into spectrograms corresponding to a plurality of subcarriers; and
   determining the physiological state information according to a frequency corresponding to a highest peak in the spectrograms;
   wherein the differences of the channel response corresponding to the time period is transformed into a first spectrogram and a second spectrogram corresponding to the subcarriers by using two frequency analysis modes, and the step of determining the physiological state information according to a frequency corresponding to the highest peak in the spectrograms further comprises:
   obtaining a first frequency corresponding to the highest peak of a vertical axis in the first spectrogram of each subcarrier and a second frequency corresponding to the highest peak of the vertical axis in the second spectrogram of each subcarrier;
   determining whether a frequency difference between the first frequency and the second frequency of a first subcarrier of the subcarriers exceeds a threshold;
   removing the first subcarrier when determining that the frequency difference exceeds the threshold, or reserving the first subcarrier when determining that the frequency difference does not exceed the threshold; and
   determining the physiological state information according to the frequencies corresponding to a highest magnitude peak in the spectrograms corresponding to the reserved subcarrier(s).

2. The method for measuring physiological state information based on channel state information as claimed in claim 1, wherein the first receiving antenna of the receiving antennas receives a first reflected signal and a second reflected signal, and the second receiving antenna of the receiving antennas receives a third reflected signal and a fourth reflected signal;
   wherein the first reflected signal is generated by reflecting a first measurement signal transmitted by the first transmitting antenna of the transmitting antennas through the target object, and the second reflected signal is generated by reflecting a second measurement signal transmitted by the second transmitting antenna of the transmitting antennas through the target object; and
   wherein the third reflected signal is generated by reflecting the first measurement signal transmitted by the first transmitting antenna through the target object, and the fourth reflected signal is generated by reflecting the second measurement signal transmitted by the second transmitting antenna through the target object.

3. The method for measuring physiological state information based on channel state information as claimed in claim 2, wherein the step of obtaining physiological state information of the target object according to the CSI further comprises:

calculating a first phase difference between the first reflected signal and the third reflected signal;

calculating a second phase difference between the second reflected signal and the fourth reflected signal; and obtaining the physiological state information of the target object according to a difference of a channel response between the first phase difference and the second phase difference.

4. A system for measuring physiological state information based on channel state information, comprising:

a transmitter, configured with at least two transmitting antennas, wherein the at least two transmitting antennas respectively transmit a measurement signal;

a receiver, configured with at least two receiving antennas, wherein each of the receiving antennas receives a reflected signal reflected the measurement signal through a target object, and the receiver obtains channel state information (CSI) between the transmitting antennas and the receiving antennas according to the reflected signals, wherein the transmitting antennas comprises a first transmitting antenna and a second transmitting antenna, the receiving antennas comprises a first receiving antenna and a second receiving antenna, the CSI comprises first CSI between the first transmitting antenna and the first receiving antenna, second CSI between the first transmitting antenna and the second receiving antenna, third CSI between the second transmitting antenna and the first receiving antenna, and fourth CSI between the second transmitting antenna and the second receiving antenna; and a computing device, coupled to the receiver, receiving the CSI, and obtaining physiological state information of the target object according to a difference value between a difference between the first CSI and the second CSI and a difference between the third CSI and the fourth CSI, wherein the step of obtaining the physiological state information of the target object according to the difference of the channel response performed by the computing device further comprises:

obtaining the differences of the channel response corresponding to a time period;

transforming the differences of the channel response into spectrograms corresponding to a plurality of subcarriers; and determining the physiological state information according to a frequency corresponding to a highest peak in the spectrograms;

wherein the computing device transforms the differences of the channel response corresponding to the time period into a first spectrogram and a second spectrogram corresponding to the subcarriers by using two frequency analysis modes, and the step of determining the physiological state information according to a frequency corresponding to the highest peak in the spectrograms performed by the computing device further comprises:

obtaining a first frequency corresponding to the highest peak of a vertical axis in the first spectrogram of each subcarrier and a second frequency corresponding to the highest peak of the vertical axis in the second spectrogram of each subcarrier;

determining whether a frequency difference between the first frequency and the second frequency of a first subcarrier of the subcarriers exceeds a threshold;

removing the first subcarrier when determining that the frequency difference exceeds the threshold, or reserving the first subcarrier when determining that the frequency difference does not exceed the threshold; and determining the physiological state information according to the frequencies corresponding to a highest magnitude peak in the spectrograms corresponding to the reserved subcarrier(s).

5. The system for measuring physiological state information based on channel state information as claimed in claim 4, wherein the first receiving antenna of the receiving antennas receives a first reflected signal and a second reflected signal, and the second receiving antenna of the receiving antennas receives a third reflected signal and a fourth reflected signal;

wherein the first reflected signal is generated by reflecting a first measurement signal transmitted by the first transmitting antenna of the transmitting antennas through the target object, and the second reflected signal is generated by reflecting a second measurement signal transmitted by the second transmitting antenna of the transmitting antennas through the target object; and wherein the third reflected signal is generated by reflecting the first measurement signal transmitted by the first transmitting antenna through the target object, and the fourth reflected signal is generated by reflecting the second measurement signal transmitted by the second transmitting antenna through the target object.

6. The system for measuring physiological state information based on channel state information as claimed in claim 5, wherein the step of obtaining physiological state information of the target object according to the CSI performed by the computing device further comprises:

calculating a first phase difference between the first reflected signal and the third reflected signal;

calculating a second phase difference between the second reflected signal and the fourth reflected signal; and obtaining the physiological state information of the target object according to a difference of a channel response between the first phase difference and the second phase difference.

7. A device for measuring physiological state information based on channel state information, comprising:

one or more processors; and one or more computer storage media for storing one or more computer-readable instructions, wherein the processor is configured to drive the computer storage media to execute the following:

receiving channel state information (CSI) between at least two transmitting antennas of a transmitter and at least two receiving antennas of a receiver, wherein the CSI is transmitted from the receiver and is obtained by the receiver according to reflected signals; the reflected signals are generated by reflecting measurement signals transmitted by the transmitting antennas of the transmitter through a target object, and the reflected signals are received by the antennas of the receiver, wherein the transmitting antennas comprises a first transmitting antenna and a second transmitting antenna, the receiving antennas comprises a first receiving antenna and a second receiving antenna, the CSI comprises first CSI between the first transmitting antenna and the first receiving antenna, second CSI between the first transmitting antenna and the second receiving antenna, third CSI between the second transmitting antenna and the first receiving antenna, and fourth CSI between the second transmitting antenna and the second receiving antenna;

obtaining physiological state information of the target object according to a difference value between a difference between the first CSI and the second CSI and a difference between the third CSI and the fourth CSI;

wherein the step of obtaining the physiological state information of the target object according to the difference of the channel response performed by the processor further comprises:

obtaining the differences of the channel response corresponding to a time period;

transforming the differences of the channel response into spectrograms corresponding to a plurality of subcarriers; and determining the physiological state information according to a frequency corresponding to a highest peak in the spectrograms;

wherein the processor transforms the differences of the channel response corresponding to the time period into a first spectrogram and a second spectrogram corresponding to the subcarriers by using two frequency analysis modes, and the step of determining the physiological state information according to a frequency corresponding to the highest peak in the spectrograms performed by the processor further comprises:

obtaining a first frequency corresponding to the highest peak of a vertical axis in the first spectrogram of each subcarrier and a second frequency corresponding to the highest peak of the vertical axis in the second spectrogram of each subcarrier;

determining whether a frequency difference between the first frequency and the second frequency of a first subcarrier of the subcarriers exceeds a threshold;

removing the first subcarrier when determining that the frequency difference exceeds the threshold, or reserving the first subcarrier when determining that the frequency difference does not exceed the threshold; and determining the physiological state information according to the frequencies corresponding to a highest magnitude peak in the spectrograms corresponding to the reserved subcarrier(s).

8. The device for measuring physiological state information based on channel state information as claimed in claim 7, wherein the first receiving antenna of the receiving antennas receives a first reflected signal and a second reflected signal, and the second receiving antenna of the receiving antennas receives a third reflected signal and a fourth reflected signal;

wherein the first reflected signal is generated by reflecting a first measurement signal transmitted by the first transmitting antenna of the transmitting antennas through the target object, and the second reflected signal is generated by reflecting a second measurement signal transmitted by the second transmitting antenna of the transmitting antennas through the target object; and wherein the third reflected signal is generated by reflecting the first measurement signal transmitted by the first transmitting antenna through the target object, and the fourth reflected signal is generated by reflecting the second measurement signal transmitted by the second transmitting antenna through the target object.

9. The device for measuring physiological state information based on channel state information as claimed in claim 8, wherein the step of obtaining physiological state information of the target object according to the CSI performed by the processor further comprises:

calculating a first phase difference between the first reflected signal and the third reflected signal;

calculating a second phase difference between the second reflected signal and the fourth reflected signal; and obtaining the physiological state information of the target object according to a difference of a channel response between the first phase difference and the second phase difference.

10. A method for measuring physiological state information based on channel state information, comprising:

receiving channel state information (CSI) between at least two transmitting antennas of a transmitter and at least two receiving antennas of a receiver, wherein the CSI is transmitted from the receiver and is obtained by the receiver according to reflected signals; the reflected signals are generated by reflecting measurement signals transmitted by the transmitting antennas of the transmitting antennas through a target object, and the reflected signals are received by the antennas of the receiver, wherein the transmitting antennas comprises a first transmitting antenna and a second transmitting antenna, the receiving antennas comprises a first receiving antenna and a second receiving antenna, the CSI comprises first CSI between the first transmitting antenna and the first receiving antenna, second CSI between the first transmitting antenna and the second receiving antenna, third CSI between the second transmitting antenna and the first receiving antenna, and fourth CSI between the second transmitting antenna and the second receiving antenna;

obtaining physiological state information of the target object according to a difference value between a difference between the first CSI and the second CSI and a difference between the third CSI and the fourth CSI;

wherein the step of obtaining the physiological state information of the target object according to the difference of the channel response further comprises:

obtaining the differences of the channel response corresponding to a time period;

transforming the differences of the channel response into spectrograms corresponding to a plurality of subcarriers; and determining the physiological state information according to a frequency corresponding to a highest peak in the spectrograms;

wherein the differences of the channel response corresponding to the time period is transformed into a first spectrogram and a second spectrogram corresponding to the subcarriers by using two frequency analysis modes, and the step of determining the physiological state information according to a frequency corresponding to the highest peak in the spectrograms further comprises:

obtaining a first frequency corresponding to the highest peak of a vertical axis in the first spectrogram of each subcarrier and a second frequency corresponding to the highest peak of the vertical axis in the second spectrogram of each subcarrier;

determining whether a frequency difference between the first frequency and the second frequency of a first subcarrier of the subcarriers exceeds a threshold;

removing the first subcarrier when determining that the frequency difference exceeds the threshold, or reserving the first subcarrier when determining that the frequency difference does not exceed the threshold; and determining the physiological state information according to the frequencies corresponding to the highest magnitude peak in the spectrograms corresponding to the reserved subcarrier(s).

11. The method for measuring physiological state information based on channel state information as claimed in claim 10, wherein the first receiving antenna of the receiving antennas receives a first reflected signal and a second reflected signal, and the second receiving antenna of the receiving antennas receives a third reflected signal and a fourth reflected signal;

wherein the first reflected signal is generated by reflecting a first measurement signal transmitted by the first transmitting antenna of the transmitting antennas through the target object, and the second reflected signal is generated by reflecting a second measurement signal transmitted by the second transmitting antenna of the transmitting antennas through the target object; and wherein the third reflected signal is generated by reflecting the first measurement signal transmitted by the first transmitting antenna through the target object, and the fourth reflected signal is generated by reflecting the second measurement signal transmitted by the second transmitting antenna through the target object;

wherein the step of obtaining physiological state information of the target object according to the CSI further comprises:

calculating a first phase difference between the first reflected signal and the third reflected signal;

calculating a second phase difference between the second reflected signal and the fourth reflected signal; and obtaining the physiological state information of the target object according to a difference of a channel response between the first phase difference and the second phase difference.

12. The method for measuring physiological state information based on channel state information as claimed in claim 10, wherein the first receiving antenna of the receiving antennas receives a first reflected signal and a second reflected signal, and the second receiving antenna of the receiving antennas receives a third reflected signal and a fourth reflected signal;

wherein the first reflected signal is generated by reflecting a first measurement signal transmitted by the first transmitting antenna of the transmitting antennas through the target object, and the second reflected signal is generated by reflecting a second measurement signal transmitted by the second transmitting antenna of the transmitting antennas through the target object; and wherein the third reflected signal is generated by reflecting the first measurement signal transmitted by the first transmitting antenna through the target object, and the fourth reflected signal is generated by reflecting the second measurement signal transmitted by the second transmitting antenna through the target object.

* * * * *